US009955851B2

United States Patent
Ito

(10) Patent No.: US 9,955,851 B2
(45) Date of Patent: May 1, 2018

(54) CONTACT DETECTING APPARATUS, OPTICAL MEASUREMENT APPARATUS, AND CONTACT DETECTING METHOD

(71) Applicant: OLYMPUS CORPORATION, Tokyo (JP)

(72) Inventor: Ryosuke Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/065,374

(22) Filed: Mar. 9, 2016

(65) Prior Publication Data

US 2016/0183770 A1  Jun. 30, 2016

Related U.S. Application Data

(63) Continuation of application No. PCT/JP2014/073057, filed on Sep. 2, 2014.

(Continued)

(51) Int. Cl.
*A61B 1/06* (2006.01)
*A61B 1/00* (2006.01)
(Continued)

(52) U.S. Cl.
CPC .......... *A61B 1/00055* (2013.01); *A61B 1/042* (2013.01); *A61B 1/0646* (2013.01); *A61B 1/0669* (2013.01); *A61B 1/07* (2013.01)

(58) Field of Classification Search
CPC ....... A61B 1/06; A61B 1/0646; A61B 1/0669; A61B 1/07
See application file for complete search history.

(56) References Cited

U.S. PATENT DOCUMENTS

2005/0063939 A1  3/2005  Ameer et al.
2006/0155178 A1  7/2006  Backman et al.
(Continued)

FOREIGN PATENT DOCUMENTS

JP  2009-074854 A  4/2009
JP  2009-537014 A  10/2009
(Continued)

OTHER PUBLICATIONS

Dec. 2, 2014 Search Report issued in International Patent Application No. PCT/JP2014/073057.
(Continued)

*Primary Examiner* — Allen Porter, Jr.
(74) *Attorney, Agent, or Firm* — Oliff PLC

(57) ABSTRACT

A contact detecting apparatus detects contact between a body tissue and a probe for emitting illumination light onto the body tissue and receiving return light of the illumination light scattered from the body tissue. The contact detecting apparatus includes: a laser light source that emits laser light to irradiate a specified region of the body tissue via the probe; a photoelectric conversion unit that converts light received via the probe into an electric signal; and a signal processing unit that determines whether or not there is contact between a distal end of the probe and the body tissue based on whether the electric signal includes a component of a beat signal caused by interference of the return light of the laser light scattered from each of a surface of the body tissue and a surface of the distal end of the probe.

18 Claims, 17 Drawing Sheets

Related U.S. Application Data

(60) Provisional application No. 61/876,584, filed on Sep. 11, 2013.

(51) Int. Cl.
    *A61B 1/04*     (2006.01)
    *A61B 1/07*     (2006.01)

(56) References Cited

U.S. PATENT DOCUMENTS

| | | |
|---|---|---|
| 2007/0129615 A1 | 6/2007 | Backman et al. |
| 2007/0179368 A1 | 8/2007 | Backman et al. |
| 2007/0197874 A1 | 8/2007 | Ishihara |
| 2008/0037024 A1 | 2/2008 | Backman et al. |
| 2009/0009759 A1 | 1/2009 | Backman et al. |
| 2009/0073454 A1 | 3/2009 | Ozawa |
| 2009/0079993 A1 | 3/2009 | Yatagai et al. |
| 2009/0148945 A1 | 6/2009 | Ameer et al. |
| 2009/0203977 A1 | 8/2009 | Backman et al. |
| 2009/0325859 A1 | 12/2009 | Ameer et al. |
| 2010/0053632 A1* | 3/2010 | Alphonse ............. A61B 5/0066 356/479 |
| 2010/0210952 A1* | 8/2010 | Taira ..................... A61B 1/043 600/476 |
| 2012/0322155 A1 | 12/2012 | Ameer et al. |
| 2013/0303861 A1 | 11/2013 | Backman et al. |
| 2014/0066587 A1 | 3/2014 | Ameer et al. |
| 2014/0180131 A1 | 6/2014 | Kamimura et al. |
| 2015/0099853 A1 | 4/2015 | Ameer et al. |

FOREIGN PATENT DOCUMENTS

| | | |
|---|---|---|
| JP | 2010-185782 A | 8/2010 |
| JP | 2011-240155 A | 12/2011 |
| WO | 2013/154061 A1 | 10/2013 |

OTHER PUBLICATIONS

Apr. 13, 2017 Extended European Search Report issued in European Patent Application No. 14844159.5.

\* cited by examiner

CONTACT DETECTING APPARATUS, OPTICAL MEASUREMENT APPARATUS, AND CONTACT DETECTING METHOD

CROSS-REFERENCE TO RELATED APPLICATIONS

This application is a continuation of PCT international application Ser. No. PCT/JP2014/073057 filed on Sep. 2, 2014 which designates the United States, incorporated herein by reference, and which claims the benefit of priority from U.S. provisional application No. 61/876,584 filed on Sep. 11, 2013, incorporated herein by reference.

BACKGROUND

1. Technical Field

The disclosure relates to a contact detecting apparatus for detecting contact between a body tissue and a measurement probe for emitting illumination light onto a body tissue in contact with a distal end thereof and receiving return light of the illumination light scattered from the body tissue, and to an optical measurement apparatus having the contact detecting apparatus for calculating a specific value representing characteristics of the body tissue, and to a contact detecting method.

2. Related Art

In the past, an optical measurement apparatus is known, which emits illumination light onto a body tissue, and calculates a characteristic value representing characteristics of the body tissue on the basis of a measured value of return light (scattered light) scattered from the body tissue. The optical measurement apparatus is used in combination with an endoscope for observing organs such as a digestive system. As such optical measurement apparatus, an optical measurement apparatus has been proposed, which uses LEBS (Low-Coherence Enhanced Backscattering) for detecting characteristics of a body tissue by emitting white light of low coherence of which spatial coherence length is short onto a body tissue from an illumination fiber distal end of a probe, and by using multiple light-receiving fibers to measure the intensity distribution of the return light at multiple angles (see United States Patent Application Publication No. 2010/0053632).

SUMMARY

In some embodiments, a contact detecting apparatus detects contact between a body tissue and a measurement probe configured to emit illumination light onto the body tissue which is in contact with a distal end of the measurement probe, and to receive return light of the illumination light scattered from the body tissue. The contact detecting apparatus includes: a laser light source configured to emit laser light to irradiate a specified region of the body tissue via the measurement probe; a photoelectric conversion unit configured to convert light received via the measurement probe into an electric signal; and a signal processing unit configured to determine whether or not there is contact between the distal end of the measurement probe and the body tissue based on whether the electric signal converted by the photoelectric conversion unit includes a component of a beat signal caused by interference of the return light of the laser light scattered from each of a surface of the body tissue and a surface of the distal end of the measurement probe.

In some embodiments, an optical measurement apparatus includes: a main body device including a light source unit for providing illumination light to irradiate a body tissue that is in contact with a distal end, a measurement unit for measuring return light of the illumination light scattered from the body tissue, and a calculation unit for calculating a characteristic value representing characteristics of the body tissue based on a measurement result by the measurement unit; a measurement probe detachably connected to the main body device and configured to emit the illumination light and to receive the return light of the illumination light; and the above-described contact detecting apparatus.

In some embodiments, a contact detecting method that is performed by a contact detecting apparatus is presented. The contact detecting apparatus includes a laser light source for emitting laser light for irradiating a body tissue in order to detect contact between the body tissue and a measurement probe for emitting the illumination light onto the body tissue which is in contact with a distal end of the measurement probe and receiving return light of the illumination light scattered from the body tissue. The method includes: converting light received via the measurement probe into an electric signal; and determining whether or not there is contact between the distal end of the measurement probe and the body tissue based on whether the converted electric signal includes a component of a beat signal caused by interference of the return light of the laser light scattered from each of a surface of the body tissue and a surface of the distal end of the measurement probe.

The above and other features, advantages and technical and industrial significance of this invention will be better understood by reading the following detailed description of presently preferred embodiments of the invention, when considered in connection with the accompanying drawings.

DETAILED DESCRIPTION

Exemplary embodiments of an optical measurement apparatus using LEES technique will be explained below in detail with reference to drawings, as preferred embodiments of a contact detecting apparatus, an optical measurement apparatus, and a contact detecting method according to the present invention. Note that the present invention is not limited to the embodiments. The same reference signs are used to designate the same elements throughout the drawings. The drawings are schematic, and it is to be noted that relationship between a thickness and a width of each member and a ratio of each member are different from the reality. The drawings may include portions where the ratio and the sizes are different.

First Embodiment

Figure 1:
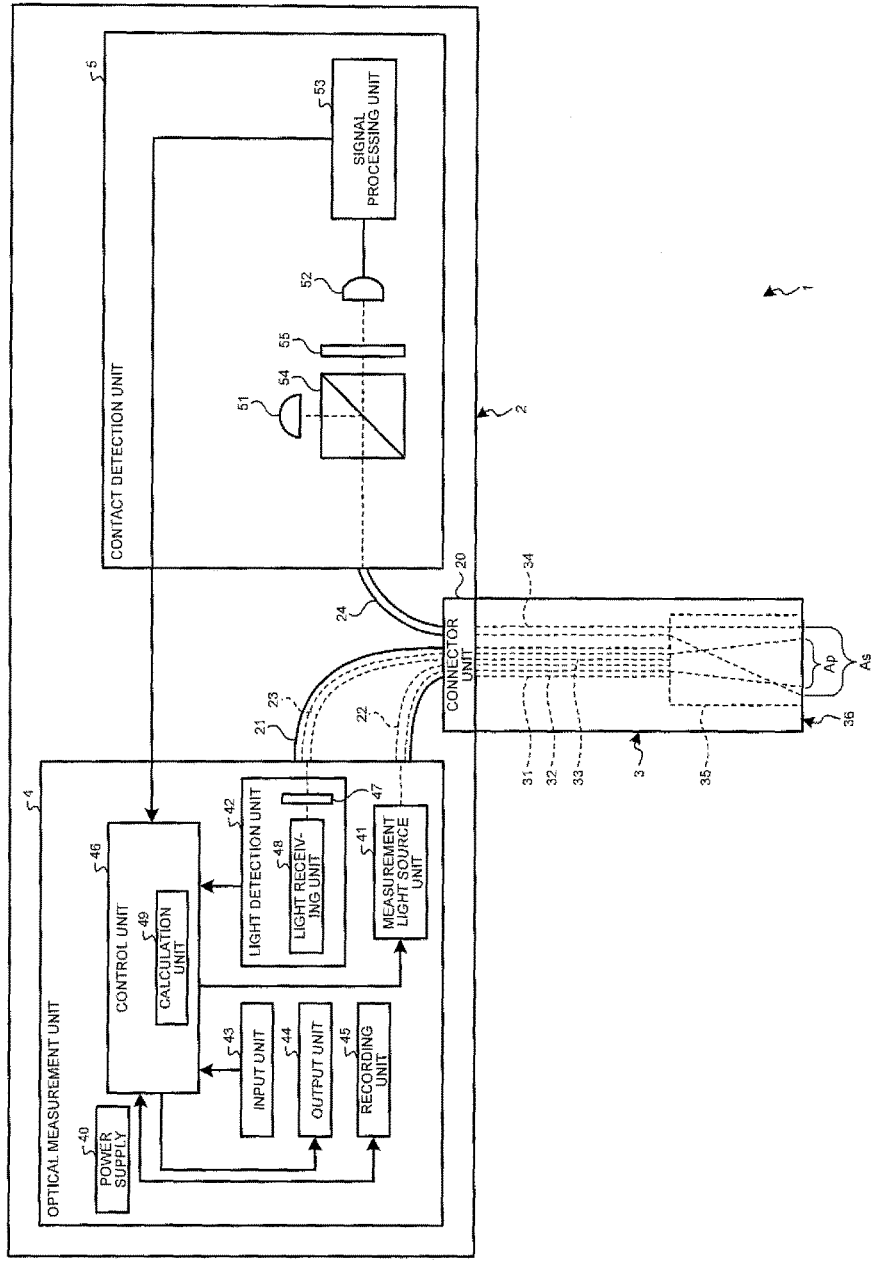
FIG. 1 is a block diagram schematically illustrating a configuration of an optical measurement apparatus according to a first embodiment of the present invention.

FIG. 1 is a block diagram schematically illustrating a configuration of an optical measurement apparatus according to a first embodiment of the present invention. The optical measurement apparatus 1 as shown in FIG. 1 includes a main body device 2 for detecting characteristics (property) of a body tissue by performing optical measurement of the body tissue which is a scattering body, and a disposable measurement probe 3 inserted into the body of a subject.

The main body device 2 includes an optical measurement unit 4 which is a measuring unit for calculating a characteristic value concerning characteristics of a body tissue, and a contact detection unit 5 for detecting contact between the body tissue and the distal end of the measurement probe 3. The main body device 2 has a connector unit 20 detachably connected to the proximal end of the measurement probe 3. The connector unit 20 is connected via a connection line 21 to an optical measurement unit 4 and is connected via a connection fiber 24 to the contact detection unit 5.

The optical measurement unit 4 includes a power supply 40, a measurement light source unit 41, a light detection unit 42, an input unit 43, an output unit 44, a recording unit 45, and a control unit 46. The power supply 40 provides electric power to each part of the optical measurement unit 4.

The measurement light source unit 41 provides illumination light of incoherent light for irradiating the body tissue, to the measurement probe 3 via the connector unit 20 and a connection fiber 22 connecting the measurement light source unit 41 and the connector unit 20. The measurement light source unit 41 is achieved with multiple lenses and an incoherent light source such as a white LED (Light Emitting Diode), a xenon lamp, a tungsten lamp, and a halogen lamp. Examples of such lenses includes a condenser lens and a collimating lens. The measurement light source unit 41 emits illumination light having a wavelength component included in a specified wavelength band. The measurement light source unit 41 provides the measurement probe 3 with illumination light of a wavelength equal to or less than 750 nm. More specifically, the measurement light source unit 41 emits, as illumination light, light having a wavelength band of red and green (for example, red: 600 nm to 750 nm, green: 500 nm to 600 nm).

Via the connector unit 20 and a connection fiber 23 connecting the light detection unit 42 and the connector unit 20, the light detection unit 42 detects return light (scattered light) of the illumination light which is made when the illumination light emitted from the measurement probe 3 is scattered (including reflection) by the body tissue, and outputs the detection result to the control unit 46. The light detection unit 42 includes a filter 47 (second filter), and a light receiving unit 48. The filter 47 passes light having a wavelength band of red and green in the return light of the illumination light. The light receiving unit 48 measures the light having the wavelength band of red and green having passed through the filter 47, and outputs the measurement result to the control unit 46. More specifically, the light receiving unit 48 detects the spectrum component and the intensity distribution of the return light of the wavelength band of red and green incident from the measurement probe 3 and having passed through the filter 47, converts the result into an electric signal, and outputs it to the control unit 46. The light receiving unit 48 is achieved with a spectrometer or a light-receiving sensor, and the like.

The input unit 43 receives input of a command signal for commanding activation of the main body device 2, a command signal for commanding start of measurement of the body tissue with the main body device 2, a command signal for commanding calibration processing, and the like, and outputs the command signals to the control unit 46. The input unit 43 is achieved using a push-type switch, a touch panel, and the like.

The output unit 44 outputs various kinds of information of the main body device 2, e.g., measurement result of a body tissue, under control of the control unit 46. The output unit 44 is achieved with a display such as liquid crystal or organic EL (Electro Luminescence), a speaker, and the like.

The recording unit 45 is achieved with a volatile memory and a non-volatile memory, and records, e.g., various kinds of data and various kinds of parameters used for the optical measurement processing and various kinds of programs for causing the main body device 2 to operate. The recording unit 45 records the detection result of the contact detection unit 5 and the measurement result of the body tissue with the optical measurement unit 4.

The control unit 46 centrally controls the main body device 2. The control unit 46 is constituted by a CPU (Central Processing Unit) and the like. The control unit 46 has a calculation unit 49. The calculation unit 49 performs multiple types of calculation processing on the basis of the measurement result with the light detection unit 42, and calculates the characteristic value concerning the characteristics of the body tissue.

The contact detection unit 5 includes a laser light source 51, a photodiode (hereinafter referred to as PD) 52, a signal processing unit 53, a beam splitter 54, and a filter 55 (first filter). A function of a photoelectric conversion unit for converting the light received with the measurement probe 3 into an electric signal is provided.

The laser light source 51 is provided separately from the measurement light source unit 41, and emits laser light having a wavelength shorter than the wavelength of the illumination light which is emitted from the measurement light source unit 41. The laser light source 51 emits laser light having a wavelength different from the wavelength of the light provided by the measurement light source unit 41. The laser light source 51 emits laser light of blue wavelength band (400 nm to 500 nm). Alternatively, the laser light source 51 emits laser light having a wavelength shorter than that of the visible light. The laser light source 51 emits laser light of a short wavelength that does not reach the inside of the body tissue and is easily reflected from the surface of the body tissue.

The PD 52 detects the return light of the laser light scattered from a distal end surface 36 of the measurement probe 3 and the surface of the body tissue, and converts it into an electric signal (analog signal).

The signal processing unit 53 converts the electric signal converted by the PD 52 from analog to digital, and analyzes the intensity and frequency of the digital electric signal, thereby detecting presence or absence of contact between the body tissue and the distal end the measurement probe 3, and outputs the detection result to the optical measurement unit 4.

The beam splitter 54 causes the laser light provided by the laser light source 51 to be incident upon the connection fiber 24, and passes the reflection light of the laser light from the body tissue surface which is emitted from the connection fiber 24, and provides it to the filter 55. The beam splitter 54 is achieved using cube type beam splitter (two triangular glass prisms are glued), plate type beam splitter (ex. glass plate), fiber coupler and optical circulator.

The filter 55 is provided at an output position of the beam splitter 54 and at an input position of the PD 52, and passes only the light having the wavelength of the laser light from among the incident light. For example, the filter 55 transmits the light of the blue wavelength band, and the PD 52 detects the light of the blue wavelength band having passed the filter 55, and converts it into an electric signal.

The measurement probe 3 includes a measurement fiber 31 having an illumination fiber 32 and a light-receiving fiber 33, a contact detection fiber 34, and a glass rod 35 which is cover glass.

The measurement fiber 31 includes the illumination fiber 32 for propagating the illumination light provided by the measurement light source unit 41 and emitting it to the body tissue, and a light-receiving fiber 33 that receives the return light of the illumination light reflected and/or scattered from the body tissue via the glass rod 35. When the LEBS technique is used, return light of at least two different scattered angles are received, and therefore, multiple light-receiving fibers are provided.

The contact detection fiber 34 causes the laser light which is emitted from the laser light source 51 to illuminate the surface of the body tissue via the contact surface of the distal end surface 36 of the measurement probe 3 and the body tissue, and propagates the reflection light of the laser light reflected from the distal end surface 36 of the measurement probe 3 and the surface of the body tissue. The contact detection fiber 34 also serves as the functions of a detection illumination fiber and a detection light-receiving fiber as recited in claims. The contact detection fiber 34 emits laser light onto a region As including at least return light measurement region Ap which is measurement region of the return light with the optical measurement unit 4 in the surface of the body tissue. As an example of the contact detection fiber 34, at least one of a single mode fiber, a multi mode fiber, and a polarization maintaining optical fiber can be employed. Among them, the polarization maintaining optical fiber is preferable for detecting the reflection light from the surface of the body tissue.

The illumination light from the measurement light source unit 41 and the return light of the illumination light scattered (including reflection) by the body tissue passes by way of the glass rod 35. Then, the laser light from the laser light source 51 also passes by way of the glass rod 35.

In this case, the signal processing unit 53 of the contact detection unit 5 detects contact between the body tissue and the distal end the measurement probe 3, on the basis of whether or not the PD 52 includes beat (light beat) component generated by the photoelectric-converted electric signal due to the Doppler effect.

Figure 2:
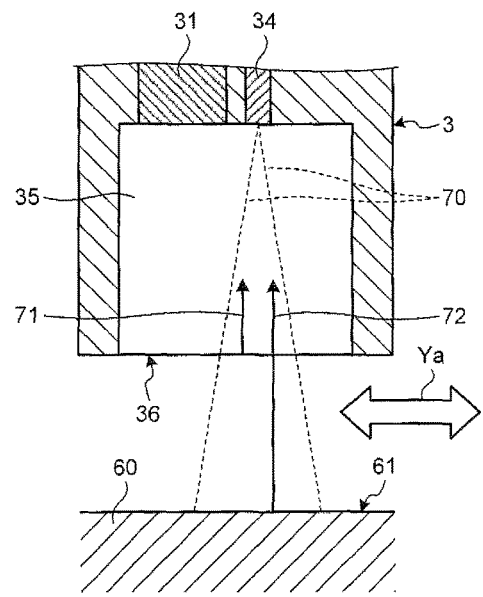
FIG. 2 is a diagram schematically illustrating a cross section, taken along the longitudinal direction, of a distal end of a measurement probe as illustrated in FIG. 1.
Figure 3:
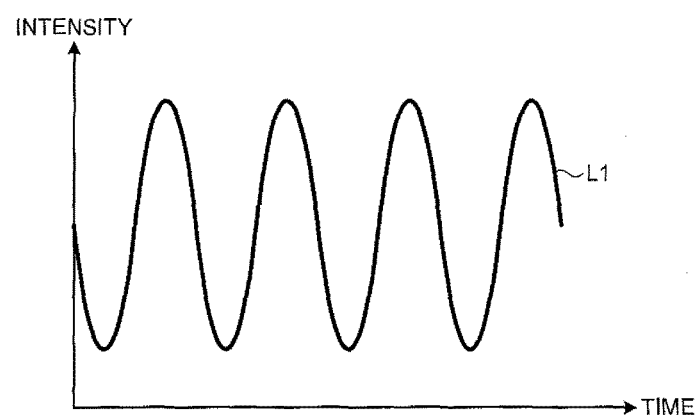
FIG. 3 is a diagram illustrating an example of an electric signal converted by PD when the distal end surface of the measurement probe and the surface of the body tissue are not in contact with each other.
Figure 4:
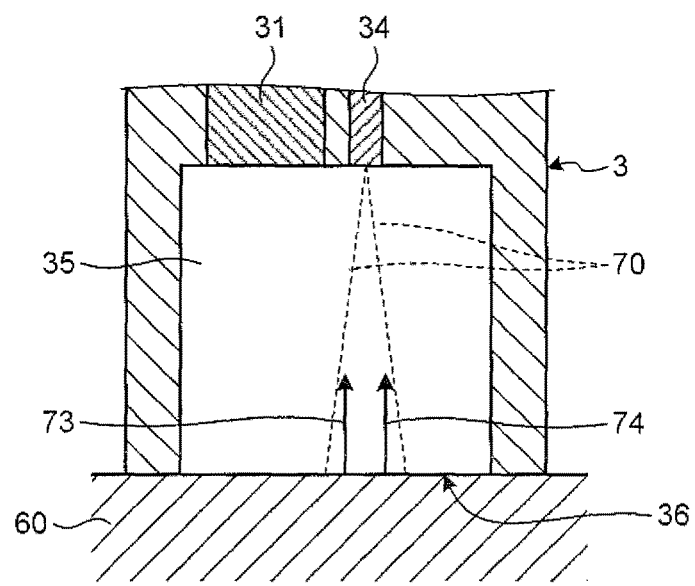
FIG. 4 is a diagram schematically illustrating a cross section, taken along the longitudinal direction, of a distal end of a measurement probe as illustrated in FIG. 1.
Figure 5:
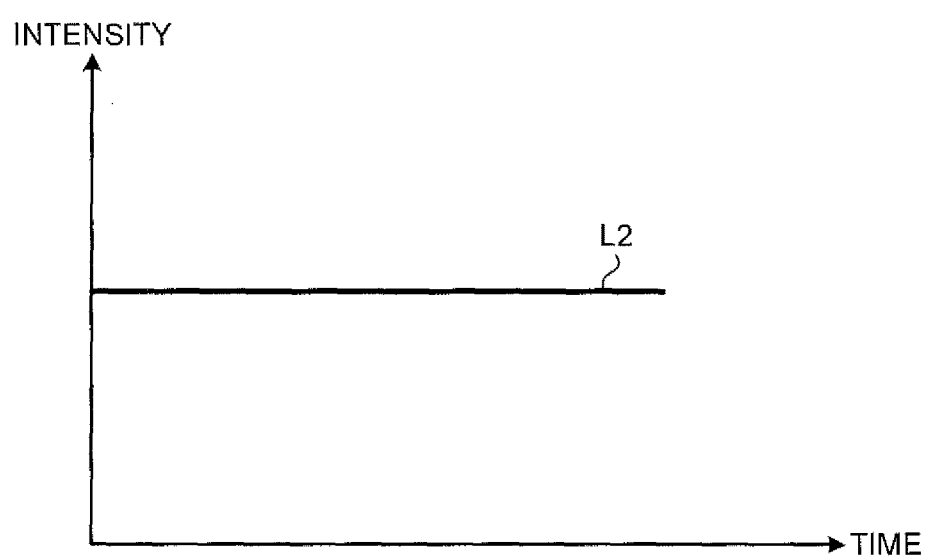
FIG. 5 is a diagram illustrating an example of an electric signal converted by a photodiode when the distal end surface of the measurement probe and the surface of the body tissue are in contact with each other.

FIGS. 2 and 4 are diagrams schematically illustrating a cross section, taken along the longitudinal direction, of a distal end of a measurement probe 3 as illustrated in FIG. 1. FIG. 2 shows a case where the distal end surface 36 of the measurement probe 3 and a surface 61 of a body tissue 60 are not in contact with each other, and FIG. 4 shows a case where the distal end surface 36 of the measurement probe 3 and the surface 61 of the body tissue 60 are in contact with each other. FIG. 3 is a diagram illustrating an example of an electric signal converted by the PD 52 when the distal end surface 36 of the measurement probe 3 and the surface 61 of the body tissue 60 are not in contact with each other. FIG. 5 is a diagram illustrating an example of an electric signal converted by the PD 52 when the distal end surface 36 of the measurement probe 3 and the surface 61 of the body tissue 60 are in contact with each other.

For example, as shown in FIG. 2, when the contact detection fiber 34 emits light 70 having a frequency f (f=c/λ, c: speed of light, λ: wavelength), return light 71 maintaining the frequency f as it is returns back to the contact detection fiber 34 from the end surface of the glass rod 35 of the distal end surface 36. However, as indicated by arrow Ya, when the distal end surface 36 of the measurement probe 3 and the surface 61 of the body tissue 60 move relatively to each other, the frequency of reflection light 72 which is the return light reflected from the surface 61 of the body tissue 60 is modulated from the frequency f by Δf due to the Doppler effect in accordance with relative moving speed of the distal end surface 36 of the measurement probe 3 and the surface 61 of the body tissue 60. As described above, when the distal end surface 36 of the measurement probe 3 and the surface 61 of the body tissue 60 move relatively to each other, interference occurs between the return light 71 from the glass rod 35 of the distal end surface 36 and the reflection light 72 reflected from the surface 61 of the body tissue 60, and the light signal which propagates through the contact detection fiber 34 and which is detected by the PD 52 includes signal having beat component (light beat signal). A curved line L1 of FIG. 3 is a diagram schematically illustrating this light beat signal.

In contrast, when, as shown in FIG. 4, the distal end surface 36 of the measurement probe 3 and the surface 61 of the body tissue 60 are in contact with each other, the distal end surface 36 of the measurement probe 3 and the surface 61 of the body tissue 60 do not move relatively to each other, and therefore, no Doppler effect occurs. Therefore, no interference occurs between return light 73 from the glass rod 35 of the distal end surface 36 and reflection light 74 reflected from the surface 61 of the body tissue 60, and no beat component occurs in the light signal which propagates through the contact detection fiber 34 and which is detected by the PD 52. For this reason, when the signal component such as noises is removed, the intensity of the light signal is substantially constant regardless of the time as shown by a straight line L2 of FIG. 5.

Figure 6:
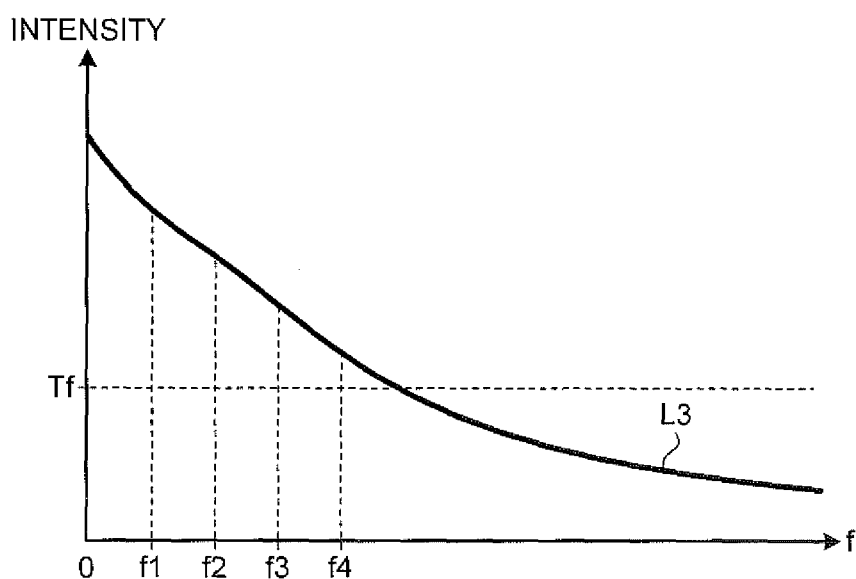
FIG. 6 is a diagram illustrating an example of an electric signal obtained by performing Fourier transform with a signal processing unit when the distal end surface of the measurement probe and the surface of the body tissue are not in contact with each other.
Figure 7:
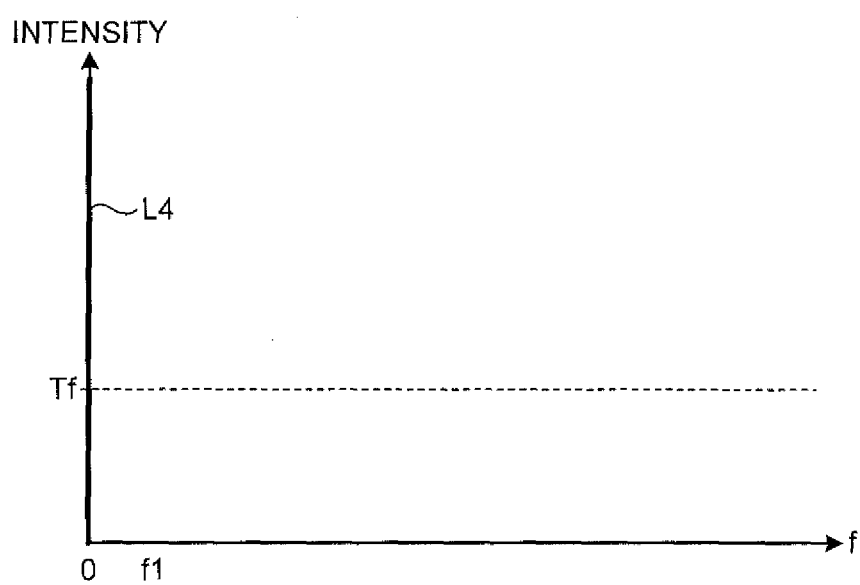
FIG. 7 is a diagram illustrating an example of an electric signal obtained by performing Fourier transform with a signal processing unit when the distal end surface of the measurement probe and the surface of the body tissue are in contact with each other.

The signal processing unit 53 performs Fourier transform processing on the electric signal detected by the PD 52, in order to determine whether the electric signal detected by the PD 52 includes the beat component or not. When the electric signal detected by the PD 52 includes beat component as shown by a curved line L1 as shown in FIG. 3, and the Fourier transform processing is performed on this electric signal, then, for example, a frequency spectrum in which the intensity changes in accordance with the frequency f can be obtained as shown by a curved line L3 as shown in FIG. 6. In contrast, when the electric signal detected by the PD 52 does not include a beat component and maintains a certain level of intensity as shown by a straight line L2 as shown in FIG. 5, and the Fourier transform processing is performed on this electric signal, then, for example, a frequency spectrum having a sharp peak where the frequency f is substantially zero can be obtained as shown by a straight line L4 as shown in FIG. 7.

For this reason, the signal processing unit 53 sets multiple sampling frequencies (four sampling frequencies, i.e., f1 to f4, in the case as shown in FIG. 6) which are expected as the modulation frequency (Δf) of the beat component, and compares the intensity (amplitude) at the sampling frequency of the frequency spectrum after the Fourier transform performed on the electric signal detected by the PD 52 with a specified amplitude threshold value (Tf in FIG. 6), thus determining the contact detection.

When at least one amplitude at the sampling frequencies of the frequency spectrum is more than the specified amplitude threshold value, the signal processing unit 53 determines that the distal end surface 36 of the measurement probe 3 and the surface 61 of the body tissue 60 are not in contact with each other. This corresponds to a case where the distal end surface 36 of the measurement probe 3 and the surface 61 of the body tissue 60 move relatively to each other since the electric signal detected by the PD 52 includes beat component.

In contrast, when all the amplitudes at the sampling frequencies of the frequency spectrum is equal to or less than the specified amplitude threshold value, the signal processing unit 53 determines that the distal end surface 36 of the measurement probe 3 and the body tissue 60 are in contact with each other. This corresponds to a case where the distal end surface 36 of the measurement probe 3 and the surface 61 of the body tissue 60 do not move relatively to each other, and more specifically corresponds to a case where the distal end surface 36 of the measurement probe 3 and the surface 61 of the body tissue 60 are in contact with each other.

Figure 8:
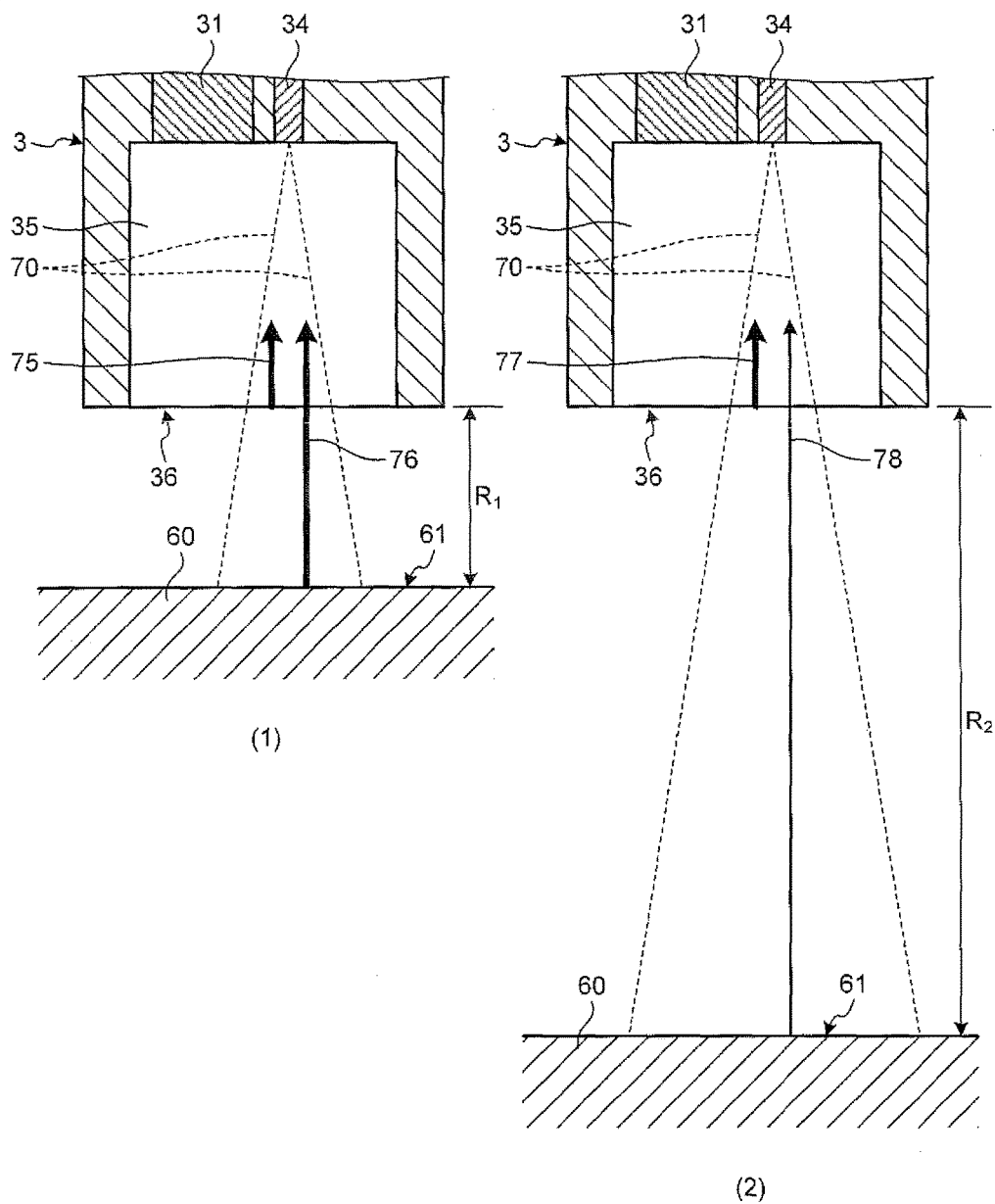
FIG. 8 is a diagram schematically illustrating reflection state of the light emitted from the measurement probe as illustrated in FIG. 1.

Subsequently, with reference to FIGS. 8 and 9, a case where the light 70 emitted from the contact detection fiber 34 is not parallel light but is spreading light will be explained. In FIG. 8, (1) indicates a situation in which a distance $R_1$ between the distal end surface 36 of the measurement probe 3 and the surface of the body tissue 60 is a distance at which contact detection can be performed on the basis of the beat component. In this situation, if beat occurs due to the interference between return light 75 and reflection light 76, then sufficient level of intensity for measurement is provided as shown by a curved line L5 as shown in (1) of FIG. 9. In contrast, (2) of FIG. 8 indicates a situation ($R_2 \gg R_1$) where a distance $R_2$ between the distal end surface 36 of the measurement probe 3 and the surface 61 of the body tissue 60 is too far. In this situation, the amount of light is attenuated before the laser light reaches the surface 61 of the body tissue 60, and therefore, even if beat occurs due to the interference between return light 77 and reflection light 78, the intensity of the beat component decreases as shown by a curved line L6 as shown in (2) of FIG. 9, and it is difficult to perform the measurement.

Accordingly, when the light 70 emitted from the contact detection fiber 34 is not parallel light but is spreading light, and the intensity of the electric signal converted by the PD 52 is less than a specified threshold value Ts (see FIG. 9), the signal processing unit 53 determines that the distal end surface 36 of the measurement probe 3 and the surface 61 of the body tissue 60 are not in contact with each other. This threshold value Ts is configured in accordance with the processing accuracy of the signal processing unit 53 so that the signal processing unit 53 can determine presence or absence of the beat component.

Figure 10:
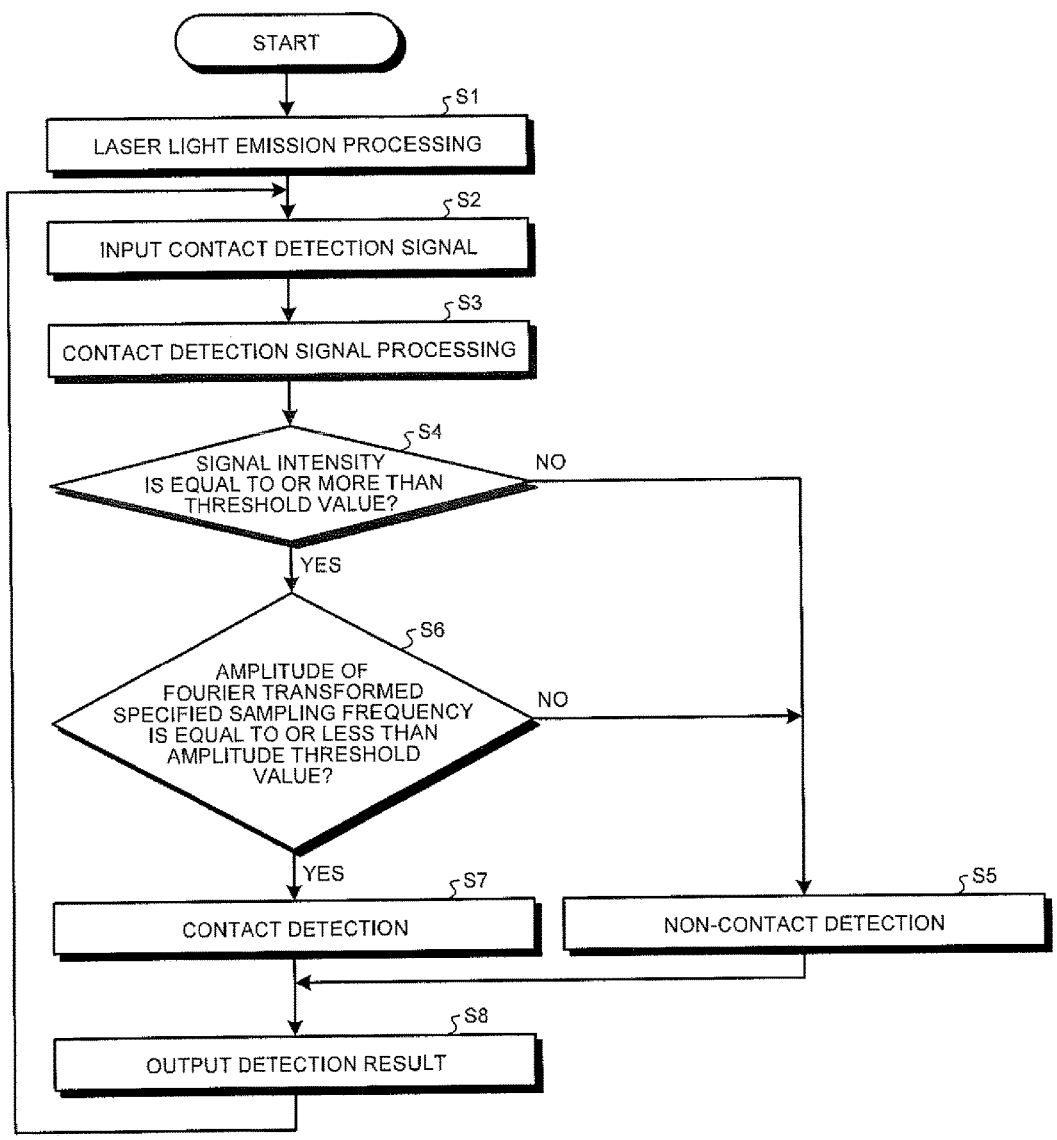
FIG. 10 is a flowchart illustrating an overview of contact detection processing for detecting presence or absence of contact between the distal end of the measurement probe and the body tissue executed by a contact detection unit as illustrated in FIG. 1.

Subsequently, contact detection processing in which the signal processing unit 53 of the contact detection unit 5 detects presence or absence of contact between the body tissue and the distal end of the measurement probe 3 will be explained. FIG. 10 is a flowchart illustrating an overview of contact detection processing for detecting presence or absence of contact between the distal end of the measurement probe 3 and the body tissue executed by a contact detection unit 5 as shown in FIG. 1. The PD 52 detects the reflection light propagated by the contact detection fiber 34 and converts it into an electric signal, and inputs it into the signal processing unit 53 as an electric signal of contact detection, with a cycle at least shorter than the measurement cycle of the return light of the optical measurement unit 4.

As shown in FIG. 10, the laser light source 51 performs laser light emission processing for emitting the laser light having a wavelength shorter than the wavelength of the illumination light onto a region As including at least a return light measurement region Ap of the optical measurement unit 4 on the surface of the body tissue, via the contact surface between the distal end surface 36 of the measurement probe 3 and the body tissue 60 (step S1). The PD 52 detects the return light from the distal end surface of the measurement probe 3 and the surface of the body tissue and converts it into an electric signal, and inputs the converted electric signal as a contact detection signal into the signal processing unit 53 (step S2).

The signal processing unit 53 performs the contact detection signal processing on the contact detection signal (step S3). In this contact detection signal processing, the signal processing unit 53 performs processing for obtaining the signal intensity of the electric signal which is input from the PD 52 and processing for obtaining the amplitude of specified sampling frequencies (for example, sampling frequencies f1 to f4 in FIG. 6) by performing Fourier transform on the electric signal.

Figure 9:
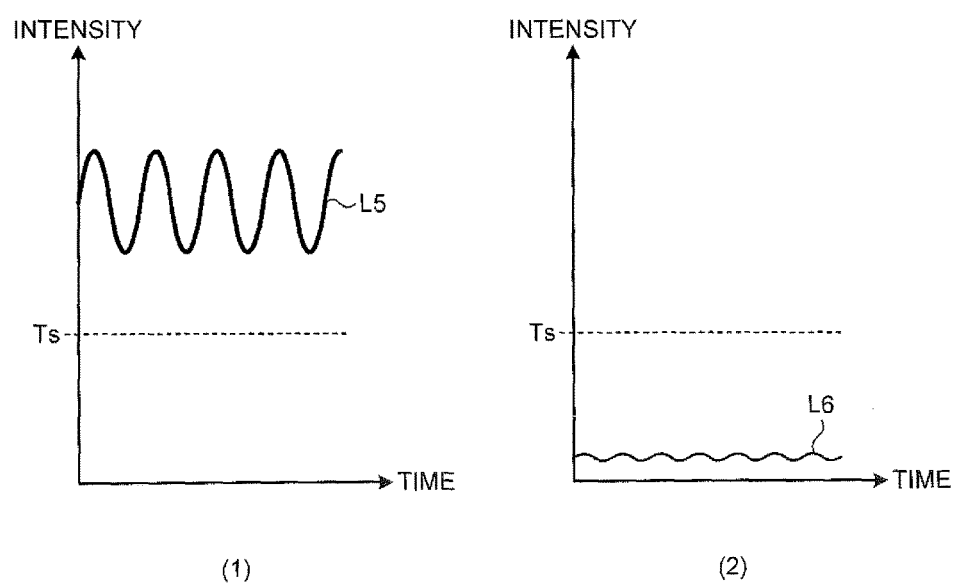
FIG. 9 is a diagram illustrating an example of an electric signal converted by a photodiode as illustrated in FIG. 1.

The signal processing unit 53 determines whether the signal intensity of the electric signal which is input from the PD 52 is equal to or more than a specified threshold value (for example, threshold value Ts as shown in FIG. 9) (step S4). When the signal intensity of the electric signal which is input from the PD 52 is determined to be less than the specified threshold value (step S4: No), the signal processing unit 53 determines that the distal end surface 36 of the measurement probe 3 and the surface 61 of the body tissue 60 are not in contact with each other (non-contact detection) (step S5).

In contrast, when the signal intensity of the electric signal which is input from the PD 52 is determined to be equal to or more than the specified threshold value (step S4: Yes), the signal processing unit 53 determines whether the amplitude of the Fourier transformed specified sampling frequency is equal to or less than the amplitude threshold value (step S6).

When the amplitude of at least one sampling frequency which has been Fourier transformed is determined to be more than the amplitude threshold value (step S6: No), the signal processing unit 53 determines that the distal end surface 36 of the measurement probe 3 and the surface 61 of the body tissue 60 are not in contact with each other (non-contact detection) (step S5).

On the other hand, when the amplitude of the Fourier transformed specified sampling frequency is determined to be equal to or less than the amplitude threshold value (step S6: Yes), the signal processing unit 53 determines that the distal end surface 36 of the measurement probe 3 and the surface 61 of the body tissue 60 are in contact with each other (contact detection) (step S7).

The signal processing unit 53 outputs the contact detection result of the distal end surface 36 of the measurement probe 3 and the body tissue 60 to the control unit 46 of the optical measurement unit 4 (step S8), and subsequently step S2 is performed.

Figure 11:
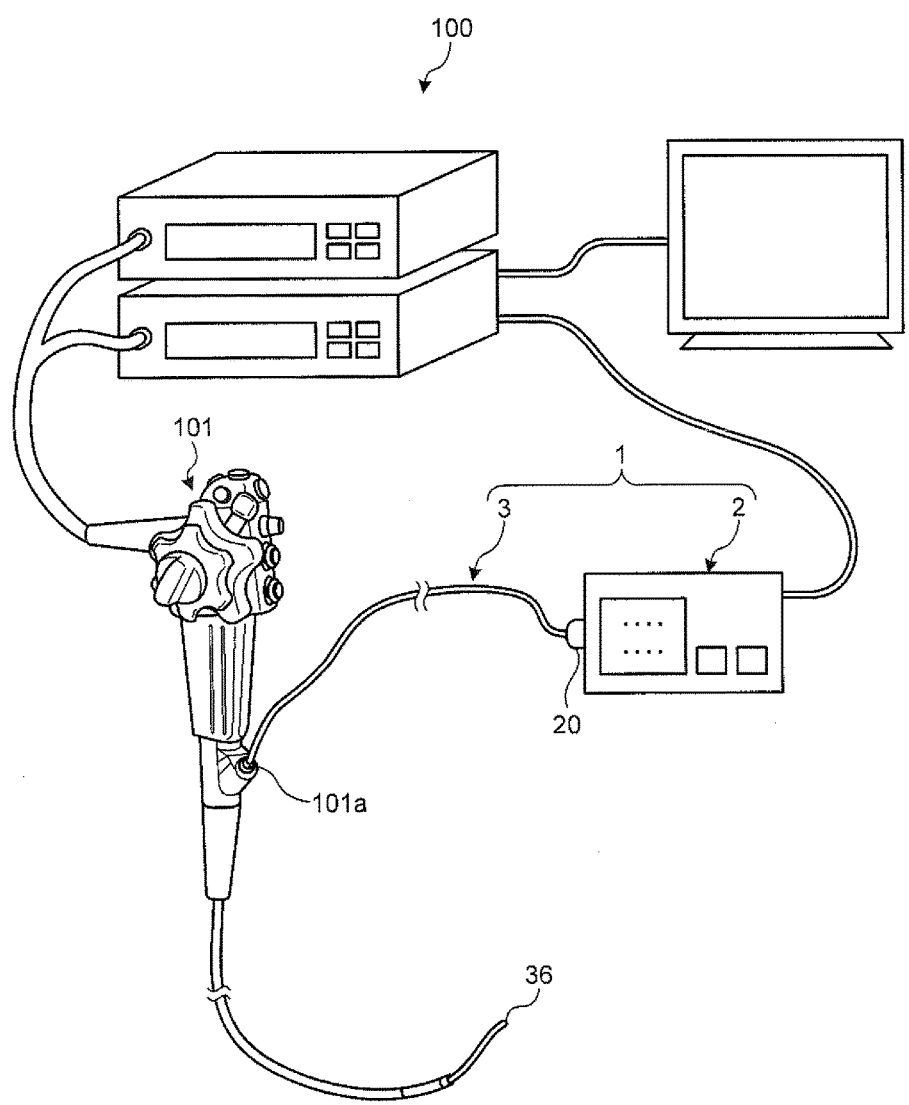
FIG. 11 is a diagram illustrating the state when the optical measurement apparatus according to the first embodiment of the present invention is used with an endoscope system.

As shown in FIG. 11, the optical measurement apparatus 1 configured as described above is configured such that the measurement probe 3 is inserted into a subject via the treatment instrument channel 101a provided in an endoscope device 101 (endoscope) of an endoscope system 100, and the illumination fiber 32 emits illumination light onto the body tissue, and the light-receiving fiber 33 detects the return light of the illumination light which has been reflected and/or scattered from the body tissue, and propagates it to the light detection unit 42. Thereafter, the calculation unit 49 calculates the characteristic value representing the characteristics of the body tissue, on the basis of the detection result detected by the light detection unit 42. The optical measurement unit 4 controls the measurement processing of the return light on the basis of the contact detection result of the body tissue 60 and the distal end surface 36 of the measurement probe 3 which is output from the contact detection unit 5. Alternatively, the optical measurement unit 4 controls the recording processing of the measurement result of the return light on the basis of the contact detection result of the body tissue 60 and the distal end surface 36 of the measurement probe 3 which is output from the contact detection unit 5.

As described above, according to the first embodiment, the characteristics of the return light from the body tissue can be obtained under the condition that the distal end surface of the measurement probe 3 and the surface of the body tissue do not move relatively to each other, by determining whether there is contact between the body tissue and the distal end of the measurement probe 3 on the basis of whether there is a component of beat caused by interference of the return light of the laser light scattered from each of the distal end surface of the measurement probe 3 and the surface of the body tissue, and thus the reliability of the measurement results of the return light of the illumination light emitted onto the body tissue can be improved.

First Modified Example of First Embodiment

Figure 12:
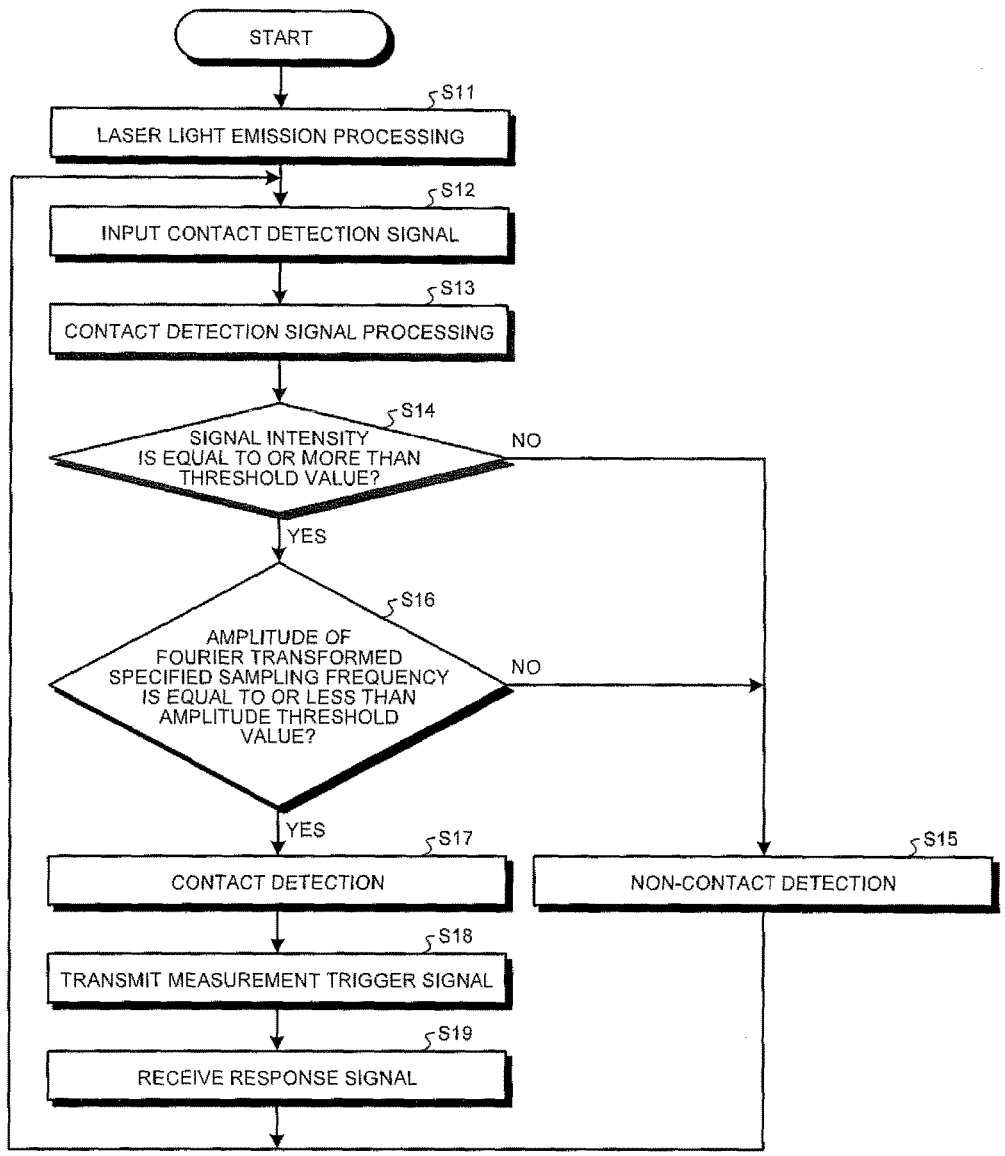
FIG. 12 is a flowchart illustrating another overview of contact detection processing for detecting presence or absence of contact between the distal end of the measurement probe and the body tissue executed by a contact detection unit according to a first modified example of the first embodiment.

FIG. 12 is a flowchart illustrating an overview of contact detection processing for detecting presence or absence of contact between the distal end of the measurement probe 3 and the body tissue executed by a contact detection unit 5 as shown in FIG. 1 as a first modified example of the first embodiment Steps S11 to S17 as shown in FIG. 12 are steps S1 to S7 as shown in FIG. 10. In step S17, when the distal end surface 36 of the measurement probe 3 and the surface 61 of the body tissue 60 are determined to be in contact with each other, the signal processing unit 53 transmits a measurement trigger signal for starting measurement of the return light to the control unit 46 of the optical measurement unit 4 (step S18). The optical measurement unit 4 receives the measurement trigger signal from the contact detection unit 5, and thereafter transmits a response signal to the contact detection unit 5, and executes the measurement of the return light. The contact detection unit 5 receives the response signal from the optical measurement unit 4 (step S19), and proceeds to step S12. The optical measurement unit 4 transmits a signal for commanding start of the measurement as a response signal, for example. Further, the optical measurement unit 4 may transmit a signal indicating that the measurement of the return light that is started after the measurement trigger signal is received has been successfully finished.

As described above, only when it is detected that the distal end surface of the measurement probe 3 and the surface of the body tissue are appropriately in contact with each other, the signal processing unit 53 may transmit the measurement trigger signal to the optical measurement unit 4, and may measure only the return light from the body tissue under the condition that the probe distal end surface and the surface of the body tissue do not move relatively to each other.

Second Modified Example of First Embodiment

Figure 13:
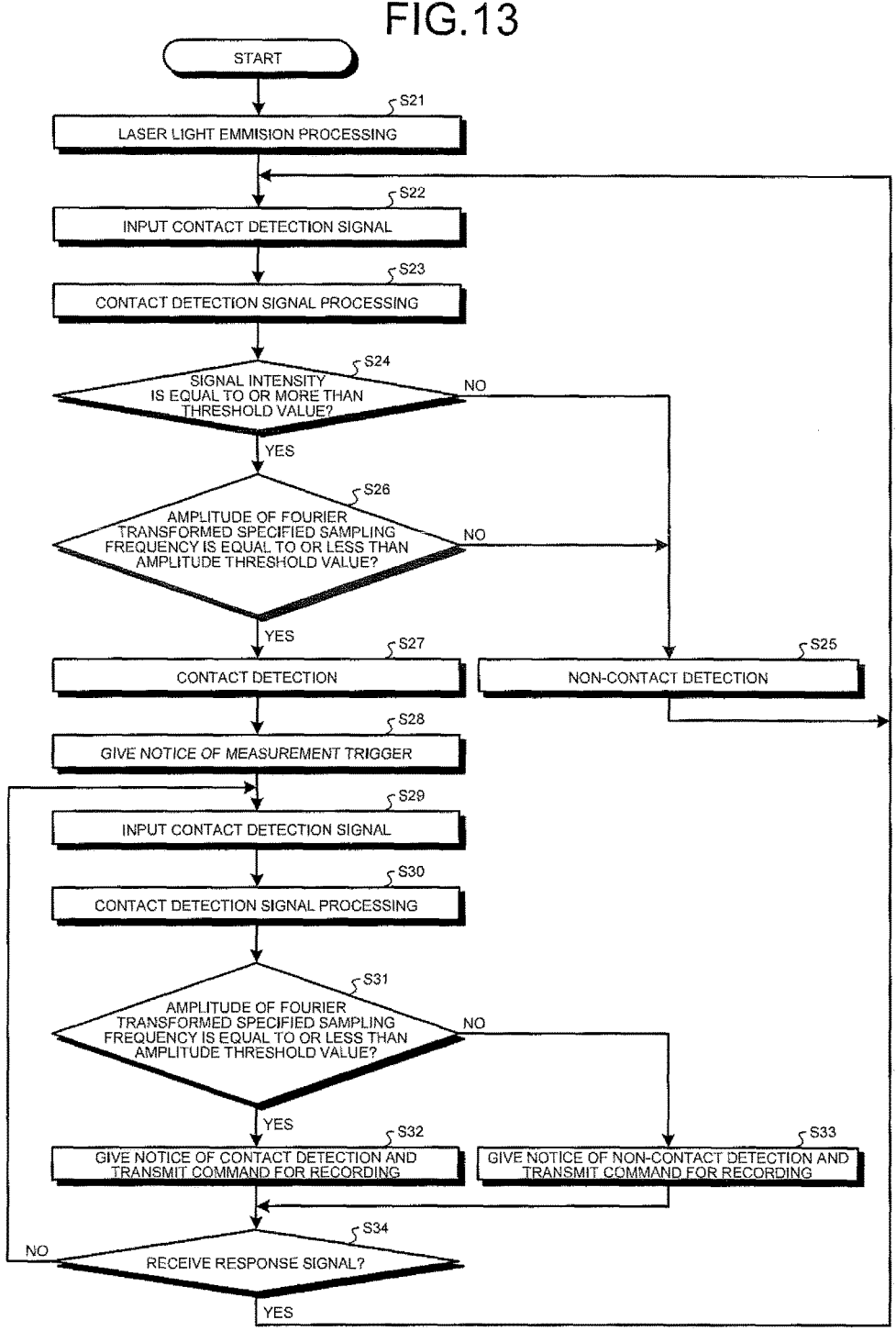
FIG. 13 is a flowchart illustrating another overview of contact detection processing for detecting presence or absence of contact between the distal end of the measurement probe and the body tissue executed by a contact detection unit according to a second modified example of the first embodiment.

FIG. 13 is a flowchart illustrating another overview of contact detection processing for detecting presence or absence of contact between the distal end of the measurement probe 3 and the body tissue executed by a contact detection unit 5 as shown in FIG. 1 as a second modified example of the second embodiment.

Steps S21 to S27 shown in FIG. 13 are identical to steps S1 to S7 shown in FIG. 10, respectively. Step S28 in FIG. 13 is step S18 in FIG. 12. In the second modified example, even while the optical measurement unit 4 is measuring the return light, the signal processing unit 53 monitors whether the distal end surface of the measurement probe 3 and the surface 61 of the body tissue are appropriately in contact with each other. When the signal processing unit 53 receives the electric signal of the contact detection from the PD 52 (step S29), the signal processing unit 53 performs contact detection signal processing in which Fourier transform is performed on the electric signal and the amplitude of the specified sampling frequency is obtained (step S30).

Subsequently, like step S6 as shown in FIG. 10, the signal processing unit 53 determines whether the amplitude of the Fourier transformed specified sampling frequency is equal to or less than the amplitude threshold value or not (step S31).

When the amplitude of the Fourier transformed specified sampling frequency is determined to be equal to or less than the amplitude threshold value (step S31: Yes), the signal processing unit 53 transmits, to the optical measurement unit 4, information indicating that the measurement probe 3 and the body tissue 60 are in contact with each other and a command for recording the information and the measurement result in the recording unit 45 in association with each other (step S32).

When the amplitude of the Fourier transformed specified sampling frequency is determined to be more than the amplitude threshold value (step S31: No), the signal processing unit 53 transmits, to the optical measurement unit 4, information indicating that the measurement probe 3 and the body tissue 60 are not in contact with each other and a command for recording the information and the measurement result in the recording unit 45 in association with each other (step S33).

Then, the signal processing unit 53 determines whether a response signal indicating that the measurement has been finished from the optical measurement unit 4 (step S34). When the signal processing unit 53 determines that the response signal is not received from the optical measurement unit 4 (step S34: No), the signal processing unit 53 returns back to step S29, and continues monitoring. When the signal processing unit 53 determines that the response signal is received from the optical measurement unit 4 (step S34: Yes), the signal processing unit 53 returns back to step S22.

As described above, even while the optical measurement unit 4 is measuring the return light, the signal processing unit 53 monitors whether the distal end surface of the measurement probe 3 and the surface of the body tissue are appropriately in contact with each other, and the contact detection result and the measurement result of the return light are associated with each other and stored, whereby the reliability of the measurement result of the return light can be further improved.

Third Modified Example of First Embodiment

Figure 14:
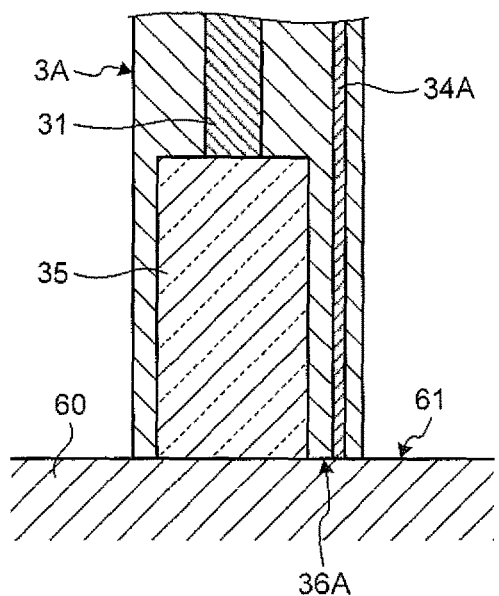
FIG. 14 is a diagram schematically illustrating a cross section, taken along the longitudinal direction, of a distal end of a measurement probe according to a third modified example of the first embodiment.

FIG. 14 is a diagram schematically illustrating a cross section, taken along the longitudinal direction, of a distal end of a measurement probe according to a third modified example of the first embodiment. The third modified example of the first embodiment is structured such that, like a measurement probe 3A as shown in FIG. 14, a contact detection fiber 34A is extended to a distal end surface 36A of the measurement probe 3A, and the laser light can be directly emitted from the distal end surface 36A of the measurement probe 3A to the surface of the body tissue 60.

Fourth Modified Example of First Embodiment

Figure 15:
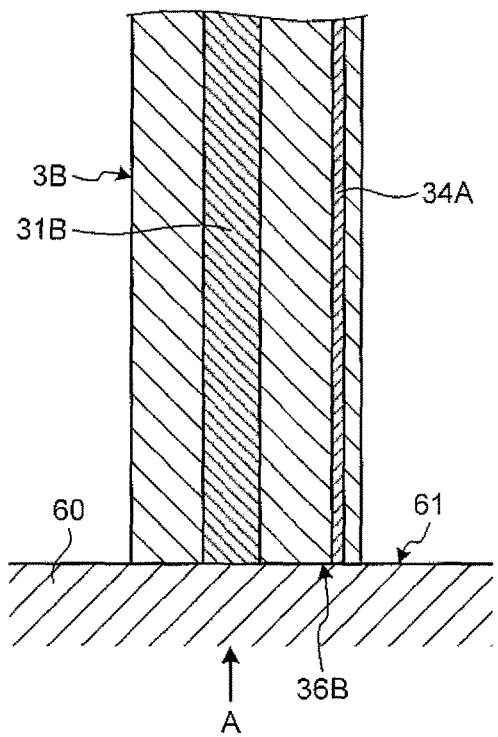
FIG. 15 is a diagram schematically illustrating a cross section, taken along the longitudinal direction, of a distal end of a measurement probe according to a fourth modified example of the first embodiment.
Figure 16:
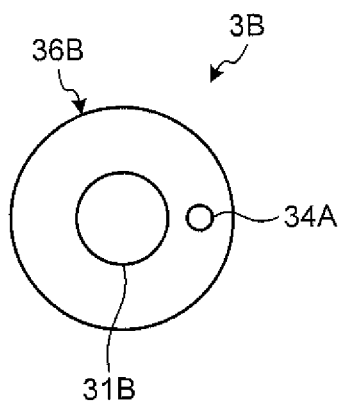
FIG. 16 is a diagram viewed from "A" of FIG. 15.

FIG. 15 is a diagram schematically illustrating another example of a cross section, taken along the longitudinal direction, of a distal end of a measurement probe according to a fourth modified example of the first embodiment. FIG. 16 is a diagram viewed from "A" of FIG. 15. In the fourth modified example of the first embodiment, like a measurement probe 3B as shown in FIGS. 15 and 16, the glass rod is deleted, and a measurement fiber 31B is also extended to a distal end surface 36B of the measurement probe 3B.

Figure 17:
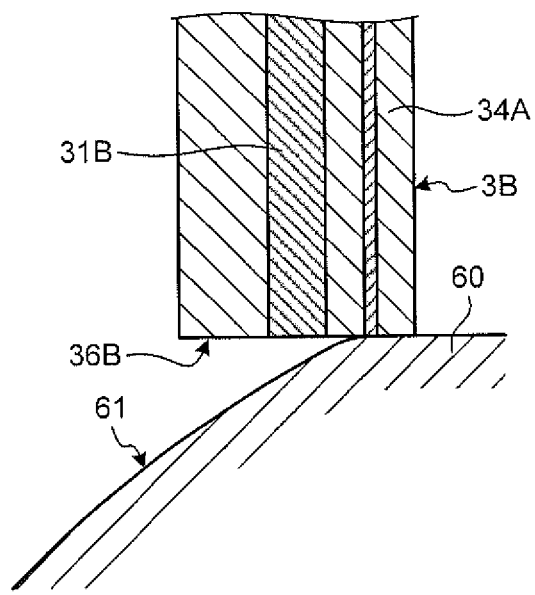
FIG. 17 is a schematic view for explaining the contact state of the measurement probe as illustrated in FIG. 15.

As shown in FIG. 17, even when the distal end surface 36B of the measurement probe 3B is partially in contact with the surface 61 of the body tissue 60, and the end surface of the measurement fiber 31B and the surface 61 of the body tissue 60 are not in contact with each other, it may be determined that the distal end surface 36B of the measurement probe 3B and the surface 61 of the body tissue 60 are in contact with each other. Therefore, multiple contact detection fibers 34A may be provided.

Fifth Modified Example of First Embodiment

Figure 18:
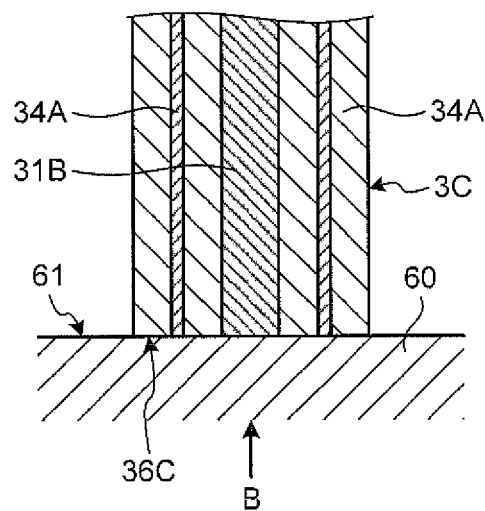
FIG. 18 is a diagram schematically illustrating a cross section, taken along the longitudinal direction, of a distal end of a measurement probe according to a fifth modified example of the first embodiment.
Figure 19:
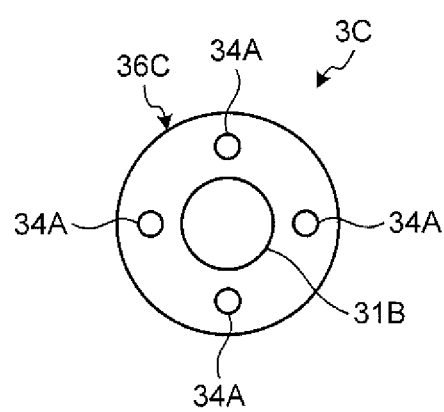
FIG. 19 is a diagram viewed from "B" of FIG. 18.

FIG. 18 is a diagram schematically illustrating another example of a cross section, taken along the longitudinal direction, of a distal end of a measurement probe according to a fifth modified example of the first embodiment. FIG. 19 is a diagram viewed from "B" of FIG. 18. A measurement probe 3C as illustrated in FIGS. 18 and 19, four contact detection fibers 34A are arranged around the measurement fiber 31B in a distributed manner. In this case, in the contact detection unit 5, the laser light source 51 provides laser light to the four contact detection fibers 34A, and the PD 52 collectively detects, as the reflection light of the laser light, the light propagated from the four contact detection fiber 34A. Then, when at least one of the four contact detection fibers 34A is non-contact with the surface 61 of the body tissue 60, beat component appears in the light signal detected by the PD 52, and therefore, the contact detection unit 5 can reliably detect whether all the surface of a distal end surface 36C of the measurement probe 3C is in contact with the surface 61 of the body tissue 60.

Second Embodiment

Figure 20:
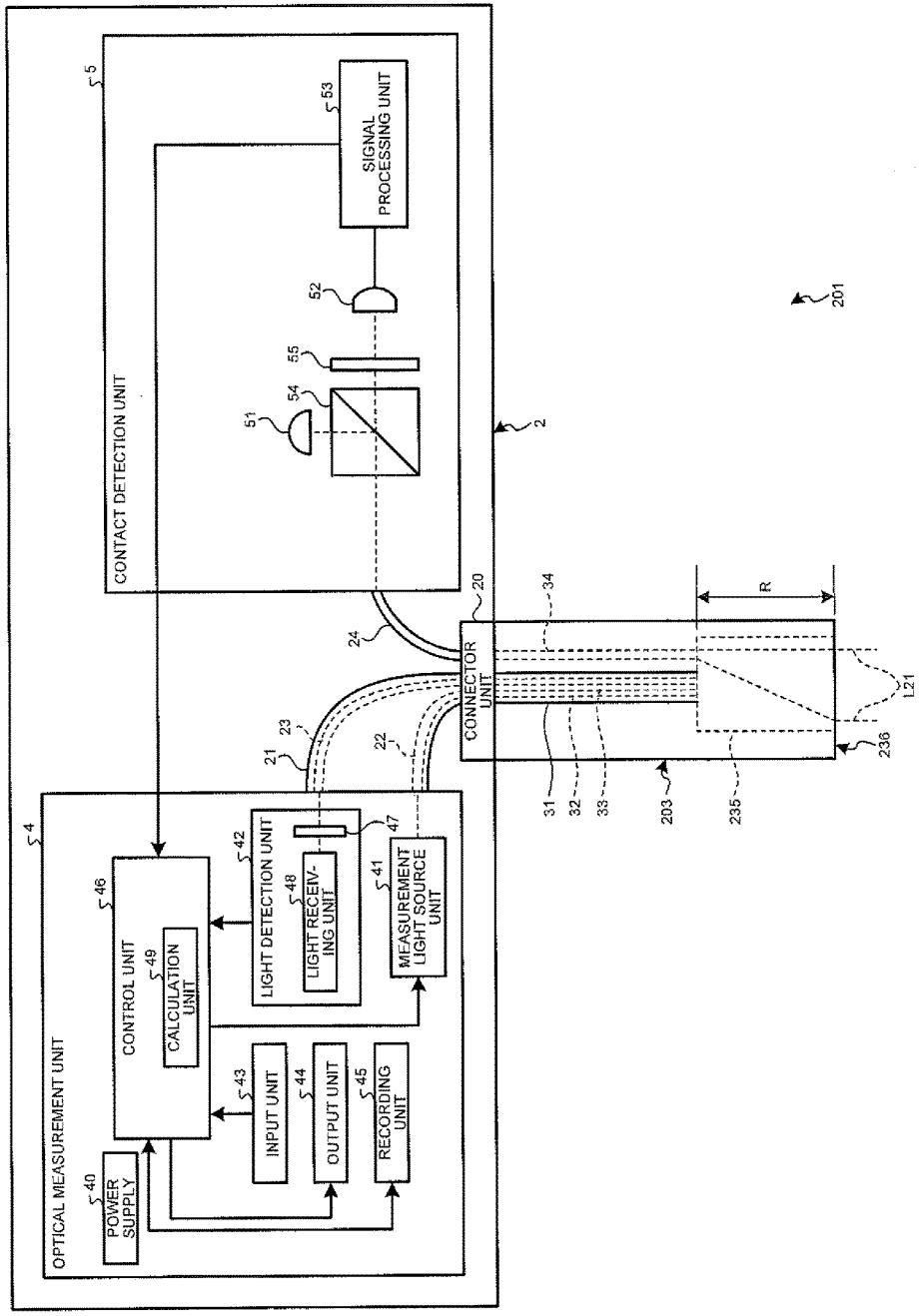
FIG. 20 is a block diagram schematically illustrating a configuration of an optical measurement apparatus according to a second embodiment.

Subsequently, the second embodiment will be explained. FIG. 20 is a block diagram schematically illustrating a configuration of an optical measurement apparatus according to the second embodiment.

As shown in FIG. 20, an optical measurement apparatus 201 according to the second embodiment includes a measurement probe 203 having a collimating lens 235 instead of the glass rod 35 of the optical measurement apparatus 1 as shown in FIG. 1. For this reason, the laser light emitted from a distal end surface 236 of the measurement probe 203 is made into parallel light L21, and this makes it unnecessary to consider the decrease in the amount of light of the laser light reaching the body tissue. Therefore, in the contact detection processing, the signal processing unit 53 can eliminate the processing in step S4 for determining whether the signal intensity of the electric signal which is input from the PD 52 of FIG. 10 is equal to or more than the specified threshold value, and as compared with the first embodiment, the calculation processing can be simplified.

The focal distance of the collimating lens 235 needs to be the same as the distance R between the fiber-side end surface of the collimating lens 235 and the distal end surface 236 which is the other end surface of the collimating lens 235. An example of the collimating lens 235 includes GRIN lens.

Third Embodiment

Figure 21:
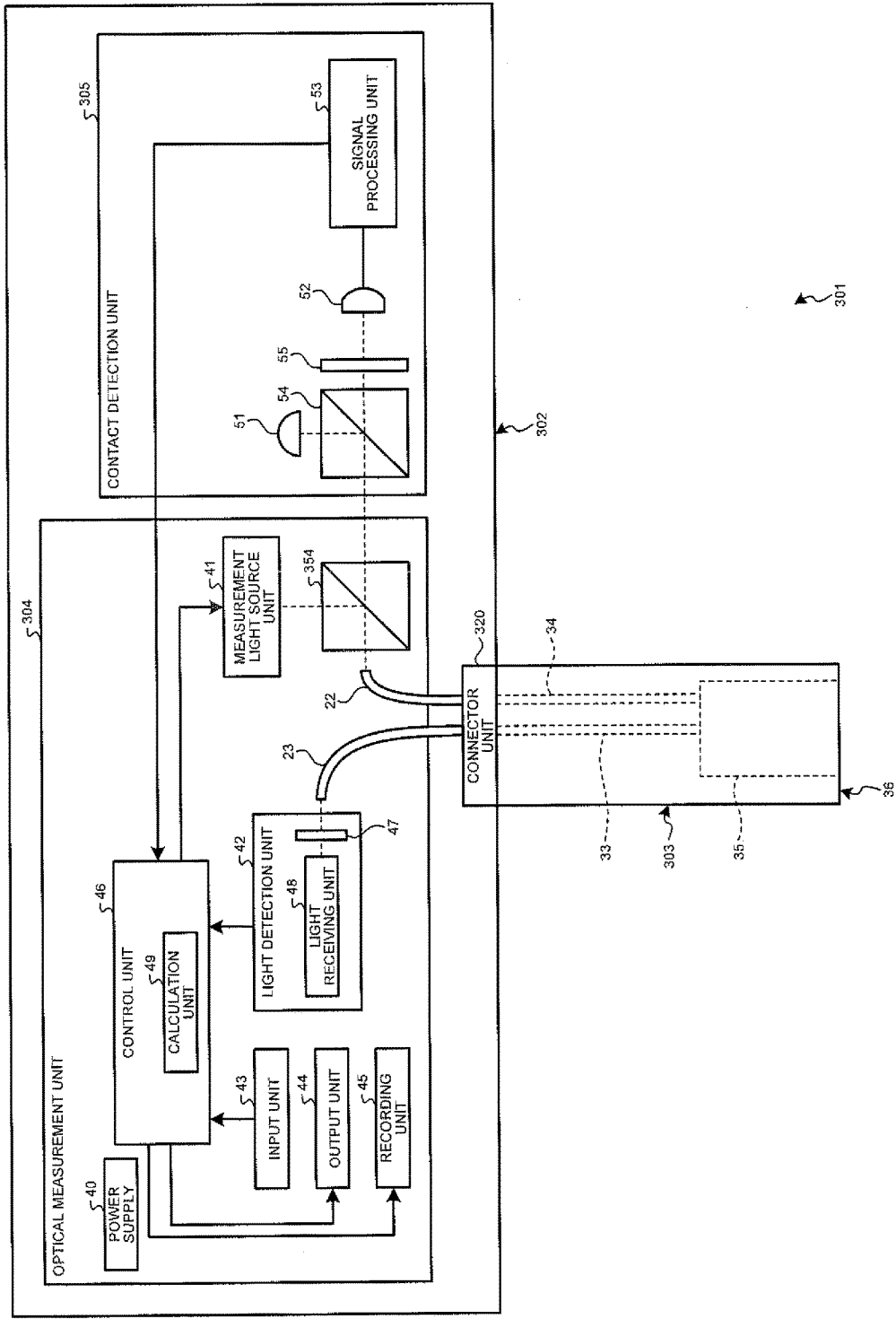
FIG. 21 is a block diagram schematically illustrating a configuration of an optical measurement apparatus according to a third embodiment.

Subsequently, the third embodiment will be explained. FIG. 21 is a block diagram schematically illustrating a configuration of an optical measurement apparatus according to the third embodiment.

As shown in FIG. 21, an optical measurement apparatus 301 according to the third embodiment is based on the optical measurement apparatus 1 as shown in FIG. 1, but is configured such that a beam splitter 354 is added to an optical measurement unit 304 of a main body device 302, and a connection fiber 24 connecting a contact detection unit 305 and a connector unit 320 is deleted. Further, in the optical measurement apparatus 301, the contact detection fiber 34 of a measurement probe 303 also serves as the illumination fiber 32 of the first embodiment.

The beam splitter 354 causes the illumination light emitted from the measurement light source unit 41 to be incident upon the connection fiber 22 and passes the laser light incident from behind via the beam splitter 54 provided at the output position so as to be incident upon the connection fiber 22. The beam splitter 354 also passes the light emitted by the connection fiber 22 and provides it to the beam splitter 54. The connection fiber 22 is connected via the connector unit 320 to the contact detection fiber 34.

In the third embodiment, the contact detection fiber also has the function of the illumination fiber of the return light measurement, and therefore, the portion of the contact detection unit 5 can be added to the optical measurement unit 304 later. More specifically, the function for detecting the contact between the distal end surface of the measurement probe and the surface of the body tissue can be added to a publicly-known optical measurement apparatus.

Figure 22:
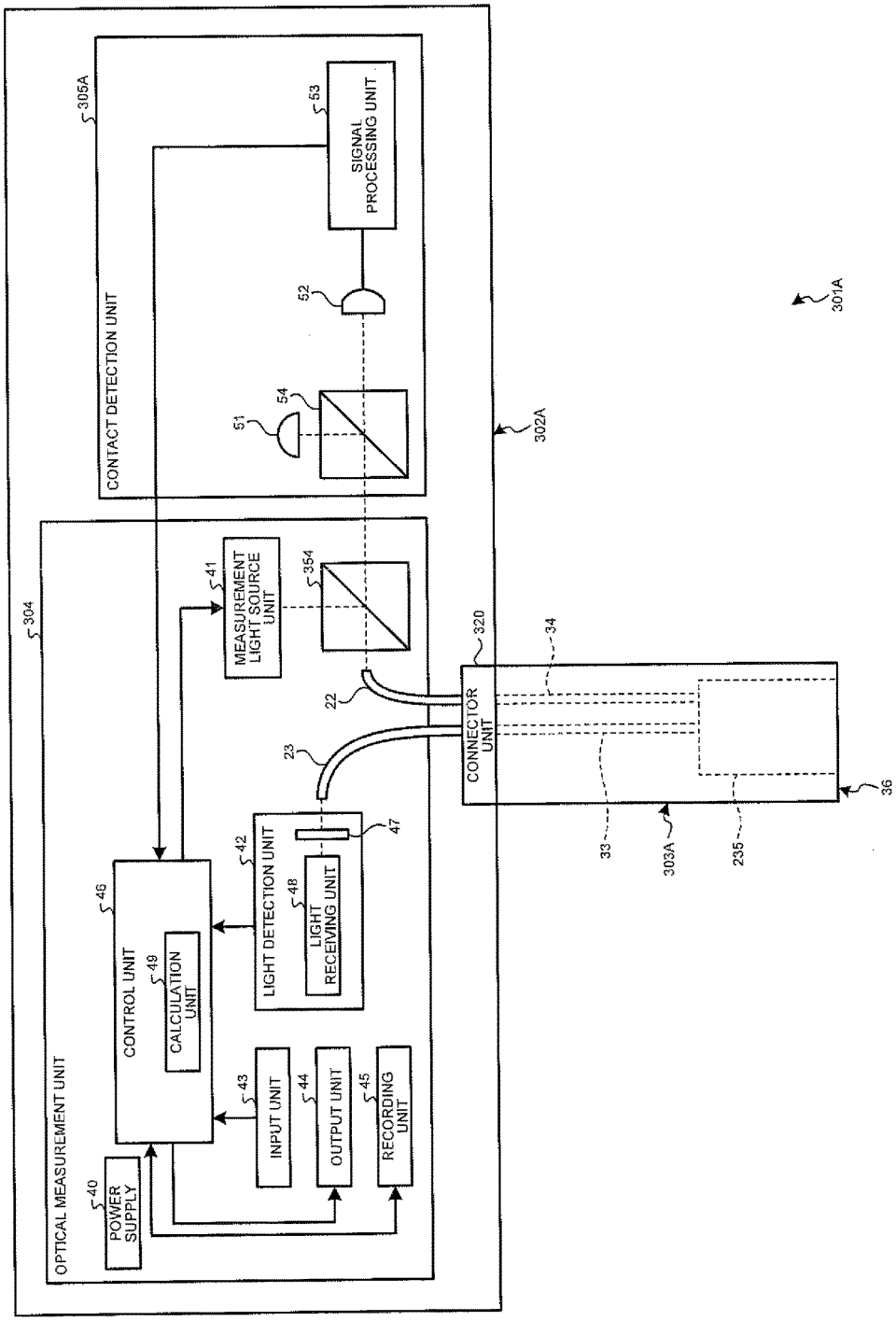
FIG. 22 is a block diagram schematically illustrating another configuration of an optical measurement apparatus according to the third embodiment.

In the third embodiment, like a measurement probe 303A of an optical measurement apparatus 301A as shown in FIG. 22, the collimating lens 235 explained in the second embodiment may be used instead of the glass rod 35. In this case, like the second embodiment, the signal processing unit 53 of a contact detection unit 305A of a main body device 302A can eliminate the processing of step S4 of FIG. 10. Further, the analog signal converted by the PD 52 is obtained by adding a certain amount of illumination light given by the measurement light source unit 41 to the reflection light of the laser light, and therefore, more specifically, without selecting the wavelength of the laser light, the beat component can be separated by only performing frequency conversion of the analog signal converted by the PD 52. Therefore, as compared with the contact detection unit 305, the contact detection unit 305A can eliminate the filter 55.

Fourth Embodiment

Figure 23:
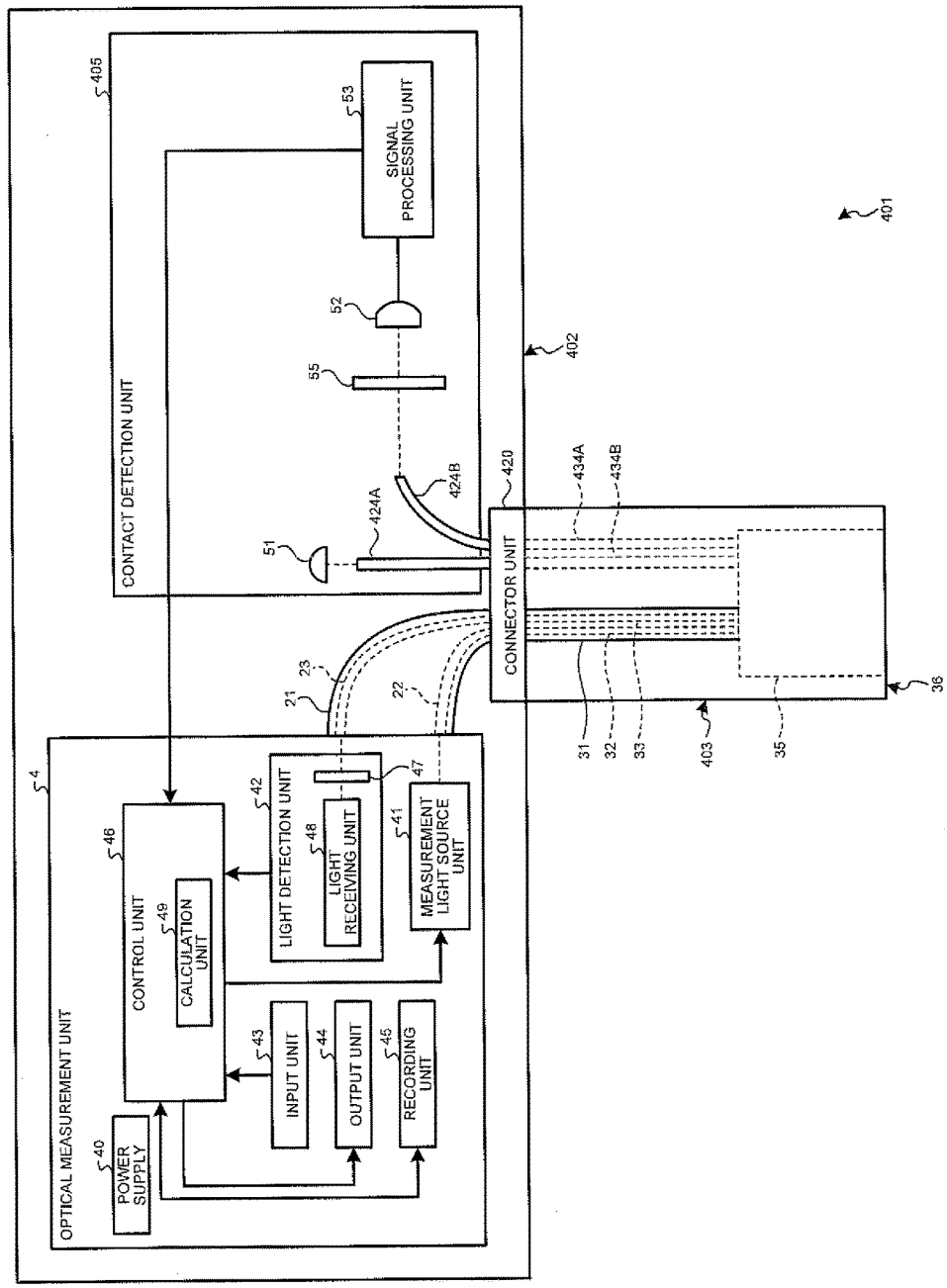
FIG. 23 is a block diagram schematically illustrating a configuration of an optical measurement apparatus according to a fourth embodiment.

Subsequently, the fourth embodiment will be explained. FIG. 23 is a block diagram schematically illustrating a configuration of an optical measurement apparatus according to the fourth embodiment.

As shown in FIG. 23, an optical measurement apparatus 401 according to the fourth embodiment includes a measurement probe 403 provided with a light fiber 434A for emitting laser light emitted by the laser light source 51 onto the surface of the body tissue and a detection fiber 434B for propagating the reflection light of the laser light. A connector unit 420 of a main body device 402 propagates, via a connection fiber 424A of a contact detection unit 405, the laser light emitted by the laser light source 51 to the light fiber 434A of the measurement probe 403. Then, the connector unit 420 propagates, via a connection fiber 424B of the contact detection unit 405, the reflection light of the laser light incident from the detection fiber 434B of the measurement probe 403 to the PD 52.

In the fourth embodiment, the laser light from the laser light source 51 and the reflection light of the laser light are not separated by the beam splitter. Instead, the fiber is provided to propagate each of them, and therefore, this can reduce the loss of the amount of light of laser light and the reflection light of the laser light, and can further enhance the detection accuracy.

An execution program for each processing executed by the optical measurement apparatus of the present invention may be configured to be provided while being recorded as a file in an installable format or in an executable format to a computer-readable recording medium such as a CD-ROM, a flexible disk (FD), a CD-R, a DVD (Digital Versatile Disk), and the like, or may be provided in such a manner that each program is stored to a computer connected to a network such as the Internet to allow download via the network. Alternatively, the execution program may be configured to be provided or distributed via a network such as the Internet.

According to some embodiments, by determining whether or not there is contact between a body tissue and a distal end of a measurement probe based on whether there is a component of a beat signal caused by interference of return light of laser light scattered from each of a surface of a distal end of the measurement probe and a surface of the body tissue, it is possible to obtain characteristics of the return light from the body tissue under the condition that the surface of the distal end of the measurement probe and the surface of the body tissue do not move relatively to each other, and to improve the reliability of the measurement results of the return light of the illumination light emitted onto the body tissue.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A contact detecting apparatus for detecting contact between a body tissue and a measurement probe configured to emit illumination light onto the body tissue which is in contact with a distal end of the measurement probe, and to receive return light of the illumination light scattered from the body tissue, the contact detecting apparatus comprising:
 a laser light source configured to emit the illumination light onto the body tissue via the measurement probe;
 a photoelectric conversion unit configured to convert the received return light of the illumination light scattered from the body tissue via the measurement probe into an electric signal; and
 a signal processing unit configured to determine whether or not there is contact between the distal end of the measurement probe and the body tissue based on whether the electric signal converted by the photoelectric conversion unit includes a component of a beat signal, the contact being determined based on the beat signal not being included in the electric signal and non-contact being determined based on the beat signal existing in the electrical signal, the beat signal being caused by interference of the return light scattered from each of a surface of the body tissue and a surface of the distal end of the measurement probe, a frequency of the return light scattered from the surface of the body tissue being modulated due to Doppler Effect in accordance with relative movement of the distal end surface of the measurement probe and the surface of the body tissue.

2. The contact detecting apparatus according to claim 1, wherein the signal processing unit is configured to:
   analyze a relationship between an amplitude and a frequency of the beat signal;
   determine that the distal end of the measurement probe and the body tissue are in contact with each other in response to the amplitude of the beat signal at a specified frequency band being equal to or less than a specified amplitude threshold value, which is set based on a processing accuracy of the signal processing unit in order to determine a presence or absence of the beat signal when the distal end of the measurement probe and the body tissue are in contact with each other; and
   determine that the distal end of the measurement probe and the body tissue are not in contact with each other in response to the amplitude at the specified frequency band being more than the specified amplitude threshold value.

3. The contact detecting apparatus according to claim 2, wherein when the signal processing unit determines that the distal end of the measurement probe and the body tissue are in contact with each other, the signal processing unit is configured to transmit a measurement trigger signal for starting measurement of the return light to a measuring unit that is connected to the measurement probe for providing the measurement probe with the illumination light, receiving the return light from the measurement probe, and calculating a characteristic value representing characteristics of the body tissue.

4. The contact detecting apparatus according to claim 3, wherein when the signal processing unit detects the contact between the distal end of the measurement probe and the body tissue during the measurement by the measuring unit, the signal processing unit transmits, to the measuring unit, information indicating the contact and a command for recording the information in association with a measurement result, and when the signal processing unit detects that the distal end of the measurement probe and the body tissue are not in contact with each other during the measurement by the measuring unit, the signal processing unit transmits, to the measuring unit, information indicating non-contact and a command for recording the information in association with a measurement result.

5. The contact detecting apparatus according to claim 1, wherein the signal processing unit is configured to:
   compare a total amplitude of the electric signal with a specified amplitude threshold value, which is set based on a processing accuracy of the signal processing unit in order to determine the presence or absence of the beat signal;
   determine that the distal end of the measurement probe and the body tissue are not in contact with each other in response to the total amplitude being less than the specified threshold value;
   determine that the distal end of the measurement probe and the body tissue are in contact with each other in response to the total amplitude being equal to or more than the specified threshold value, and in response to an amplitude of the beat signal at a specified frequency band being equal to or less than a specified amplitude threshold value; and
   determine that the distal end of the measurement probe and the body tissue are not in contact with each other in response to the total amplitude is equal to or more than the specified threshold value and in response to the amplitude of the beat signal at the specified frequency band being more than the specified amplitude threshold value.

6. The contact detecting apparatus according to claim 5, wherein when the signal processing unit determines that the distal end of the measurement probe and the body tissue are in contact with each other, the signal processing unit is configured to transmit a measurement trigger signal for starting measurement of the return light to a measuring unit that is connected to the measurement probe for providing the measurement probe with the illumination light, receiving the return light from the measurement probe, and calculating a characteristic value representing characteristics of the body tissue.

7. The contact detecting apparatus according to claim 6, wherein when the signal processing unit detects the contact between the distal end of the measurement probe and the body tissue during the measurement by the measuring unit, the signal processing unit transmits, to the measuring unit, information indicating the contact and a command for recording the information in association with a measurement result, and when the signal processing unit detects that the distal end of the measurement probe and the body tissue are not in contact with each other during the measurement by the measuring unit, the signal processing unit transmits, to the measuring unit, information indicating non-contact and a command for recording the information in association with a measurement result.

8. The contact detecting apparatus according to claim 1, wherein the laser light source is configured to emit the illumination light having different wavelengths.

9. The contact detecting apparatus according to claim 1, further comprising a first filter that is provided at an input position of the photoelectric conversion unit and is configured to pass only light having a wavelength of the illumination light from among incident light.

10. An optical measurement apparatus comprising:
   the contact detecting apparatus according to claim 1;
   a main body device including the laser light source for providing illumination light to irradiate the body tissue that is in contact with a distal end of the main body;
   a measurement unit for measuring return light of the illumination light scattered from the body tissue; and
   a calculation unit for calculating a characteristic value representing characteristics of the body tissue based on a measurement result by the measurement unit;
   a measurement probe detachably connected to the main body device and configured to emit the illumination light and to receive the return light of the illumination light.

11. The optical measurement apparatus according to claim 10, wherein the measurement probe comprises:
   a detection illumination fiber configured to irradiate a specified region on the surface of the body tissue with the illumination light emitted by the laser light source; and a detection light-receiving fiber configured to receive and propagate at least the return light of the illumination light scattered from each of the surface of the distal end of the measurement probe and the surface of the body tissue.

12. The optical measurement apparatus according to claim 11, wherein the detection illumination fiber and the detection light-receiving fiber are formed of a same fiber.

13. The optical measurement apparatus according to claim 11, wherein the detection illumination fiber is configured to further propagate and emit the illumination light from the light source unit.

14. The optical measurement apparatus according to claim 10, further comprising a cover glass provided at the distal end of the measurement probe.

15. The optical measurement apparatus according to claim 10, further comprising a collimating lens provided at the distal end of the measurement probe.

16. The optical measurement apparatus according to claim 10, further comprising a second filter that is provided at an input position of the measurement unit and is configured to pass only light having a same wavelength as that of the illumination light from among the return light.

17. The optical measurement apparatus according to claim 10, wherein the wavelength of the illumination light is equal to or less than 750 nm.

18. A contact detecting method that is performed by a contact detecting apparatus, the contact detecting apparatus including a laser light source for emitting illumination light for irradiating a body tissue in order to detect contact between the body tissue and a measurement probe for emitting the illumination light onto the body tissue which is in contact with a distal end of the measurement probe and receiving return light of the illumination light scattered from the body tissue, the method comprising:

converting the received return light of the illumination light scattered from the body tissue via the measurement probe into an electric signal; and determining whether or not there is contact between the distal end of the measurement probe and the body tissue based on whether the converted electric signal includes a component of a beat signal, the contact being determined based on the beat signal not being included in the electric signal and non-contact being determined based on the beat signal existing in the electrical signal, the beat signal caused by interference of the return light scattered from each of a surface of the body tissue and a surface of the distal end of the measurement probe, a frequency of the return light scattered from the surface of the body tissue being modulated due to Doppler Effect in accordance with relative movement of the distal end surface of the measurement probe and the surface of the body tissue.

* * * * *